United States Patent [19]

Tahara et al.

[11] Patent Number: 4,576,940
[45] Date of Patent: Mar. 18, 1986

[54] ANTI-ALLERGIC 3-INDOLECARBOXAMIDES

[75] Inventors: Tetsuya Tahara; Tsuguo Ikebe; Michio Terasawa; Tomonori Imayoshi, all of Oita, Japan

[73] Assignee: Yoshitomi Pharmaceutical Industries, Ltd., Osaka, Japan

[21] Appl. No.: 639,292

[22] Filed: Aug. 10, 1984

[30] Foreign Application Priority Data

Sep. 14, 1983 [JP] Japan .................. 58-170061

[51] Int. Cl.$^4$ .................. A61K 31/55; A61K 31/445; C07D 401/12
[52] U.S. Cl. .................. 514/212; 260/239 B; 260/245.7; 514/323; 514/414; 546/201; 546/223; 548/467; 548/557
[58] Field of Search .................. 546/201; 548/467; 260/245.7; 514/212, 323, 414

[56] References Cited

U.S. PATENT DOCUMENTS 2,814,625 11/1957 Speeter et al. .................. 546/201
3,527,761 9/1970 Archibald et al. .................. 546/201
4,064,255 12/1977 Champseix et al. .................. 546/201

FOREIGN PATENT DOCUMENTS 1255928 11/1961 France .................. 546/201
1345872 2/1974 United Kingdom .................. 546/201

OTHER PUBLICATIONS

Archibald, J. et al., *J. Med. Chem.*, 1971, 14(11), 1054–1059.

March, *Advanced Organic Chemistry*, 1st Ed., McGraw-Hill, 1968, p. 336.

*Primary Examiner*—Richard A. Schwartz
*Attorney, Agent, or Firm*—Sughrue, Mion, Zinn, Macpeak & Seas

[57] ABSTRACT

3-Indolecarboxamide compounds of the formula:

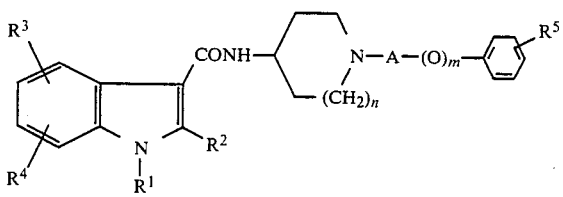

inclusive of pharmaceutically acceptable acid addition salt and/or hydrate forms thereof, wherein $R^1$ is $C_{1-8}$ alkyl, $C_{3-8}$ cycloalkyl, $C_{3-8}$ cycloalkyl-$C_{1-8}$ alkyl, allyl, propargyl, or phenyl or phenyl-$C_{1-4}$ alkyl which may be optionally substituted, on the benzene ring, by at least one substituent selected from the group consisting of halogen, trifluoromethyl, $C_{1-4}$ alkyl and $C_{1-4}$ alkoxy; $R^2$ is H or $C_{1-6}$ alkyl; $R^3$ is H, halogen, $C_{2-6}$ alkanoyloxy, benzoyloxy, $C_{1-4}$ alkoxy, benzyloxy, hydroxy or $C_{1-4}$ alkyl; $R^4$ is H, halogen, $C_{1-4}$ alkyl, $C_{1-4}$ alkoxy or hydroxy; $R^5$ is H or $C_{1-4}$ alkoxy; A is ethylene or trimethylene, which may be optionally substituted by $C_{1-4}$ alkyl; n is zero, 1 or 2; and m is zero or 1, are useful as drugs for the prevention and treatment of various allergic diseases.

11 Claims, No Drawings

ANTI-ALLERGIC 3-INDOLECARBOXAMIDES

FIELD OF THE INVENTION

The present invention relates to novel and therapeutically valuable compounds and pharmaceutical composition which comprises of at least one compound of the present invention.

DESCRIPTION OF THE PRIOR ART

Among the allergic reactions provoked by the disorders of immunoreaction, it is known that the so-called Type I reaction, one of the immediate hypersensitivity types, is caused by IgE antigen and is one of the causes of asthmatic attacks. Further, it is recognized that the Type I reaction occurs as a result of release of histamine or slow reacting substance of anaphylaxis (hereinafter referred to as SRS-A) and so on from the various cells by the antigen-antibody reaction.

Recently, the metabolic pathways of arachidonic acid and the chemistry of the metabolites, which are known as "arachidonic acid cascade", have been significantly elucidated, and it has been clarified that aliphatic peroxides and leukotrienes (hereinafter referred to as LTs) which are formed as metabolites by the action of 5-lipoxygenase play important roles in inflammation and allergy.

LTs such as $LTC_4$, $LTD_4$ or $LTE_4$ have strong bronchoconstriction activity, and it was proved that these LTs are the same substance as SRS-A.

Since these LTs induced allergic reactions are not antagonized by conventional antihistaminic drugs, compounds having 5-lipoxygenase inhibiting activity are known to be useful for the treatment of allergic tracheal and bronchial or pulmonary diseases, allergic shocks or other various allergic diseases.

It is reported that an antiasthmatic activity is synergistically potentiated with the simultaneous treatment of an anti-SRS-A drug and antihistaminic drug.

Therefore, development of compounds which possess both 5-lipoxygenase inhibiting activity and antihistaminic activity and which are useful in the prevention and treatment of various allergic diseases such as asthma or allergic rhinitis has been desired.

G.B. Pat. No. 1,345,872 discloses amino- and acylaminopyridine and -hydropyridine derivatives including 1-[2-(3-benz[g]-indolyl)ethyl]-4-benzamidopiperidine. Such derivatives exhibit anti-inflammatory activity and/or action on the cardiovascular system and/or anti-histamine activity and sometimes central nervous system activity.

U.S. Pat. No. 3,527,761 discloses 3-[2-(4-[indole-3-carboxamido]-1-piperidyl)ethyl]indole which exhibits moderate hypotensive effect, very weak anti-histaminic activity and effective anti-inflammatory action.

3-[2-(4-benzamidoperid-1-yl)ethyl]indole (indoramin) which possesses hypotensive activity is disclosed in the Journal of Medicinal Chemistry, 1971, Vol. 14, No. 11, page 1054–1059.

According to the present inventor's investigations, none of these prior art compounds exhibit 5-lipoxygenase inhibiting activity.

SUMMARY OF THE INVENTION

As a result of various investigations, the present inventors have found that novel 3-indolecarboxamide compounds and pharmaceutically acceptable acid addition salts thereof, and hydrates thereof exhibit both 5-lipoxygenase inhibiting activity and antihistaminic activity and are useful for the prevention and treatment of various allergic diseases.

DETAILED DESCRIPTION OF THE INVENTION

The 3-indolecarboxamide compounds of the present invention are represented by the following formula:

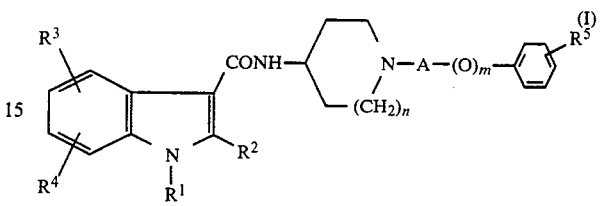

wherein $R^1$ is a $C_{1-8}$ alkyl group (e.g. methyl, ethyl, propyl, isopropyl, butyl, isobutyl, pentyl, isopentyl, hexyl, heptyl or octyl), a $C_{3-8}$ cycloalkyl group (e.g. cyclopropyl, cyclobutyl, cyclopentyl, cyclohexyl or cycloheptyl), a $C_{3-8}$ cycloalkyl-$C_{1-8}$ alkyl group (e.g. cyclopropylmethyl, cyclobutylmethyl, cyclopentylmethyl, cyclohexylmethyl, cycloheptylmethyl, 2-cyclohexylethyl, 3-cyclohexylpropyl, 4-cyclohexylbutyl, 5-cyclobutylpentyl, 6-cyclopentylhexyl or 7-cycloheptylheptyl), an allyl group, a propargyl group, or a phenyl group or phenyl-$C_{1-4}$ alkyl group which may be optionally substituted, on the benzene ring, by at least one substituent selected from the group consisting of a halogen atom (e.g. fluorine, chlorine or bromine), a trifluoromethyl group, a $C_{1-4}$ alkyl group (e.g. methyl, ethyl, propyl, butyl or tertiary butyl) and a $C_{1-4}$ alkoxy group (e.g. methoxy, ethoxy, propoxy or butoxy such as phenyl, o-chlorophenyl, m-chlorophenyl, p-chlorophenyl, p-fluorophenyl, p-bromophenyl, m-trifluoromethylphenyl, p-methylphenyl, p-tertiary butyl phenyl, p-methoxyphenyl, benzyl, p-fluorobenzyl, p-chlorobenzyl, p-methoxybenzyl, 2-phenylethyl, 2-(p-fluorophenyl)ethyl or 2-(p-methoxyphenyl)ethyl; $R^2$ is a hydrogen atom or a $C_{1-6}$ alkyl group (e.g. methyl, ethyl, propyl, butyl, isobutyl, pentyl, isopentyl, or hexyl); $R^3$ is a hydrogen atom, a halogen atom (fluorine, chlorine, bromine or iodine), a $C_{2-6}$ alkanoyloxy group (e.g. acetoxy, propionyloxy, isobutyryloxy, pivaloyloxy or hexanoyloxy), a benzoyloxy group, a $C_{1-4}$ alkoxy group (e.g. methoxy, ethoxy, propoxy or butoxy), a benzyloxy group, a hydroxyl group or a $C_{1-4}$ alkyl group (e.g. methyl, ethyl, propyl, butyl or tertiary butyl); $R^4$ is a hydrogen atom, a halogen atom (fluorine, chlorine, bromine or iodine), a $C_{1-4}$ alkyl group (e.g. methyl, ethyl, propyl, butyl or tertiary butyl), a $C_{1-4}$ alkoxy group (e.g. methoxy, ethoxy, propoxy or butoxy) or a hydroxyl group; $R^5$ is a hydrogen atom or a $C_{1-4}$ alkoxy group (e.g. methoxy, ethoxy, propoxy or butoxy); A is an ethylene group or trimethylene group, which may be optionally substituted by a $C_{1-4}$ alkyl group (e.g. methyl, ethyl, propyl or butyl); n is zero, 1 or 2; and m is zero or 1.

More preferable compounds of the formula (I) are represented by the following formula:

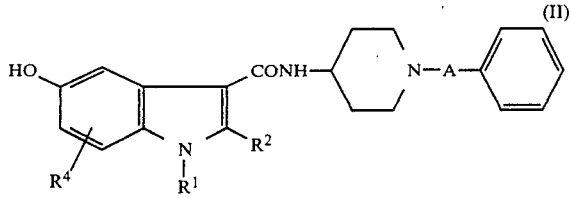

wherein $R^1$, $R^2$, $R^4$ and A are as defined above.

Most preferable compounds of the present invention are the compounds of formula (II) wherein $R^2$ is a methyl group, $R^4$ is a hydrogen atom and A is an ethylene group.

In pharmacological experiments, the compounds of the present invention show 5-lipoxygenase inhibiting activity at concentrations of 0.1–100 μM, and possess potent and long-lasting antihistaminic activity with $pA_2$ values of 7–9, but are characteristically very weak in central nervous system depressant activity which often causes drowsiness or sedation and so on. Furthermore, the compounds of the present invention do not exhibit hypotensive activity which is known to be an adverse side effect.

The compounds of formula (I) of the present invention can be prepared by reacting a carboxylic acid of the formula:

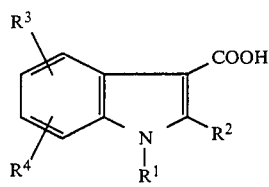

wherein each symbol is as defined above, or a functional derivative thereof with a compound of the formula:

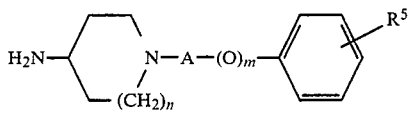

wherein each symbol is as defined above.

The reaction is carried out by a conventional amide preparation method or a peptide-synthesis method.

In case that the compounds of formula (III) are carboxylic acids, for example, the reaction is carried out in an inert solvent, under cooling, at room temperature or under heating, in the presence of a condensing agent such as dicyclohexylcarbodiimide, titanium tetrachloride, a phosphorus halide (e.g. phosphorus trichloride or phosphorus oxychloride) or diphenylphosphoryl azide.

When an acid halide (e.g. acid chloride or acid bromide) or a mixed acid anhydride (e.g. a mixed acid anhydride with a lower alkanoic acid or a mixed acid anhydride with an alkylphosphoric acid) is used as the functional derivative of the carboxylic acids of formula (III), the reaction is carried out in an inert solvent at room temperature, or under cooling or heating, preferably in the presence of a deacidifying agent such as an organic base (e.g. triethylamine or pyridine) or an inorganic base (e.g. sodium hydrogencarbonate, an alkali carbonate or an alkali hydroxide).

In case that a lower alkyl ester or so-called active ester (e.g. p-nitro-phenyl ester, p-nitrobenzyl ester or p-chlorophenyl ester) is used other functional derivative, the reaction is carried out in an inert solvent at room temperature or under refluxing, if desired, in the presence of a strong basic catalyst such as sodium alkoxide.

The compounds of formula (III) wherein at least one of $R^3$ and $R^4$ is a hydroxyl group may be used by means of the protection of the hydroxyl group with a lower alkoxy group, a benzyloxy group, a dihydropyranyloxy group, a lower alkanoyloxy group or a benzoyloxy group for the acylation of the compounds (IV) as mentioned above. And then the protecting group of the resulting compounds can be removed by treating with an acid or an alkali or subjecting to catalytic hydrogenation on palladium carbon or platinum oxide and so on, if desired.

The compounds of formula (I) thus obtained can be converted into pharmaceutically acceptable acid addition salts thereof by treating with an inorganic acid such as hydrochloric acid, hydrobromic acid, phosphoric acid, nitric acid or sulfuric acid or an organic acid such as p-toluenesulfonic acid, methanesulfonic acid, citric acid, butyric acid, maleic acid, fumaric acid or tartaric acid.

The following pharmacological experiments illustrate the potent effects of the compounds of the present invention.

1. Inhibitory activity on 5-lipoxygenase (Effect of test compounds on arachidonic acid induced chemiluminescence of peripheral leukocytes in guinea pigs)

(1) Isolation of leukocytes and preparation of leukocyte suspension

Guinea pigs were anesthetized with ethyl ether, and the peripheral blood was collected in heparinized syringes (10 U/ml, blood) from the abdominal aorta through a needle.

50 ml of a 6% dextran solution (molecular weight 177,000, Nakarai Chemicals Ltd.) was added to 100 ml of blood. This suspension was gently mixed, and was allowed to sediment for 60 minutes at room temperature. The upper leukocyte-rich suspension was centrifuged at 400×g for 10 minutes at room temperature. Tris-HCl buffer (pH 7.65) containing 5.0 ml of a 0.83% ammonium chloride solution was added to the cell pellet to lyse remaining erythrocytes. This suspension was centrifuged at 150×g for 10 minutes at 4° C. Eagle's MEM (10 ml) containing 10% fetal bovine serum (Flow Laboratories, Inc.) was added to the cell pellet. This suspension was centrifuged under the same conditions. The cell pellet was suspended in an equal volume of phosphate buffered saline (pH 7.4) containing 0.2% glucose and 0.2% bovine serum albumin, and this mixture was centrifuged under the same conditions. The above procedure was performed twice, and the cell pellet was suspended in the above buffer to adjust the leukocyte counts to $5 \times 10^6$ cells/ml.

(2) Chemiluminescence assay

Chemiluminescence was measured by the method of Yoshimoto et al. which is described in Biochem. Biophys. Res. Commun. 107, 779–784, 1982. Briefly, 0.3 ml of a leukocyte suspension was preincubated with 5 μl of a test compound solution of phosphate-buffered saline as controls, 0.05 ml of 1 mM luminol (Nakarai Chemicals, Ltd.) and 0.05 ml of 100 μM indomethacin (Sumitomo Chemical Co. Ltd.) After preincubation at 26° C. for 2 minutes, 100 μl of 2 mM arachidonic acid (Sigma) was added to the reaction mixture. Chemiluminescence was recorded continuously by an Aminco Chem-Glow model J4-7441S photometer equipped with a Hitachi model 056 recorder, and the peak height of luminol intensity was measured. The effects of test compounds were expressed as $IC_{50}$ values (μM).

(3) Results

| Test compound (No. of Example) | 5-lipoxygenase inhibiting activity $IC_{50}$ (μM) |
| --- | --- |
| 2 | 0.45 |
| 4 | 0.85 |
| 12 | 1.7 |
| 16 | 1.0 |
| 24 | 4.2 |
| 26 | 2.5 |
| 29 | 1.4 |
| 31 | 0.26 |
| Comparison A | 4.5 |

Comparison A: Nordihydroguaiaretic acid (non-specific inhibitory agent on lipoxygenase)
$IC_{50}$: median inhibition concentration 2. Inhibitory effect on histamine induced asthma in guinea pigs (1) Method The experiment was performed according to the method of Suyama et al. which is described in Jpn. J. Allergol. 15, 549–556, 1966. Female Hartley guinea pigs weighing 300–400 g were used in groups of 5 or more. One hour after the oral administration of test compound solution, animals were placed in a transparent square box and exposed to a 0.2% histamine hydrochloride (Nakarai Chemicals, Ltd.) saline aerosol using an ultrasonic nebulizer (Nihon Kohden, TUR-3000). Protection was assessed during the exposure period (5 minutes) by the presence or absence of loss of righting due to dyspnea. The effects of test compounds were expressed in terms of percent inhibition.

(2) Results

| Test compound (No. of Example) | Antihistaminic activity (% inhibition) Dose (mg/kg, p.o.) | | | |
| --- | --- | --- | --- | --- |
| | 0.5 | 2.5 | 5 | 25 |
| 2 | 40% | 100% | | |
| 4 | 60% | | | |
| 5 | 100% | | | |
| 6 | 0% | 60% | | |
| 10 | 20% | 100% | | |
| 16 | | 100% | | |
| 29 | 33% | | | |
| Comparison B | | | 20% | 100% |

Comparison B: Diphenhydramine (Antihistaminic agent)

3. Acute toxicity in mice and rats (1) Method

The acute toxicity of test compound No. 2 was evaluated in 120 male mice weighing 30–42 g and 120 female mice weighing 23–35 g, and in 56 male rats weighing 150–190 g and 56 female rats weighing 115–150 g by oral and intraperitoneal administration. The animals were observed for 14 days after administration of test compound. $LD_{50}$ values were calculated by probit method.

(2) Results

| Animals | $LD_{50}$ (mg/kg) | |
| --- | --- | --- |
| | p.o. | i.p. |
| Mice | | |
| Male | >12,000 | 1,427 (1,274–1,614)* |
| Female | >10,435 | 1,471 (1,287–1,664)* |
| Rats | | |
| Male | >9,000 | 1,943 (1,187–2,720)* |
| Female | >9,000 | 1,928 (1,400–2,748)* |

*Confidence limits of $LD_{50}$ value

In view of the results above, the compounds of the present invention are proved to be useful as a new type of anti-allergic agents, so the compounds of the present invention can be used as drugs for the prevention or treatment of various allergic diseases such as asthma or allergic rhinitis.

The compounds of the present invention can be administered as anti-allergic agent, preferably in the form of a pharmaceutical composition with a suitable and conventional carrier such as an excipient, an extender, a diluent or a solubilizer without harmful side effects to the patients.

The pharmaceutical composition can take the form of tablets, granules, powder, capsules or injectable solution. The choice of carrier is determined by the preferred form of administration, the solubility of the compound and standard pharmaceutical practice.

FORMULATION EXAMPLE 20 mg tablets are prepared from the following compositions:

| Compound 2 | 20.0 mg |
| --- | --- |
| Corn starch | 15.0 mg |
| Lactose | 66.0 mg |
| Microcrystalline cellulose | 15.0 mg |
| Talc | 3.0 mg |
| Magnesium stearate | 1.0 mg |
| | 120.0 mg |

The single dose of the compounds of the present invention for human adults usually ranges from 0.01 to 10 mg/kg depending on body weight, but it may vary depending upon the age, body weight, and/or severity of the condition to be treated as well as the response to the medication.

The present invention will be better understood from the following examples, but they are not to be construed as limiting the present invention.

EXAMPLE 1

To a suspension of 26 g of 5-acetoxy-1-butyl-2-methyl-3-indolecarboxylic acid in 300 ml of benzene was added 13 ml of thionyl chloride, and the mixture was refluxed for 3.5 hours. After the solvent and the excess thionyl chloride was distilled off, the residual crystalline acid chloride was dissolved in 400 ml of toluene. To the solution was added dropwise a solution of 18 g of 4-amino-1-(2-phenylethyl)-piperidine and 20 ml of pyridine in 80 ml of toluene under ice-cooling. Then the mixture was stirred at room temperature for 2.5 hours and the crystals precipitated were filtered with suction. The crystals were washed well with ethyl acetate to give crude 5-acetoxy-1-butyl-2-methyl-N-(1-(2-phenylethyl)-4-piperidyl)indole-3-carboxamide hydrochloride. The corresponding free base, which was recrystallized from ethyl acetate containing a small amount of methanol, melts at 170°–174° C.

EXAMPLE 2

To a solution of 2.3 g of 5-acetoxy-1-butyl-2-methyl-N-(1-(2-phenylethyl)-4-piperidyl)indole-3-carboxamide hydrochloride in 30 ml of methanol was added a solution of 0.5 g of potassium hydroxide in methanol, and the whole solution was stirred for an hour under heating. After the reaction mixture was cooled, the precipitated inorganic substance was filtered off and the filtrate was concentrated under reduced pressure. A solution of the residue in water with a small amount of ethanol was stirred and the precipitated crystals were filtered with suction. Recrystallization from ethyl acetate gave 1-butyl-5-hydroxy-2-methyl-N-(1-(2-phenylethyl)-4-piperidyl)indole-3-carboxamide as white crystals, melting at 178°–181° C. The corresponding hydrochloride monohydrate melts at 244°–247° C. with decomposition.

EXAMPLE 3

To a suspension of 25 g of 5-acetoxy-1-benzyl-2-methyl-3-indolecarboxylic acid in 400 ml of toluene was added 11 ml of thionyl chloride, and the whole mixture was heated at 70°–80° C. for 5 hours. After the completion of reaction, the reaction mixture was concentrated and the solvent was evaporated to dryness. To a solution of residue in 400 ml of toluene was added dropwise a solution of 16 g of 4-amino-1-(2-phenylethyl)piperidine in 35 ml of pyridine under cooling. After addition, the whole mixture was stirred at room temperature for 3 hours and the precipitated crystals were filtered with suction. A suspension of the crystals in 250 ml of ethyl acetate was refluxed for 2 hours. The reaction mixture was cooled on standing, and filtered with suction to give almost pure 5-acetoxy-1-benzyl-2-methyl-N-(1-(2-phenylethyl)-4-piperidyl)indole-3-carboxamide hydrochloride.

EXAMPLE 4

To a solution of 7.6 g of potassium hydroxide in 500 ml of methanol was added 37 g of the hydrochloride obtained in Example 3, and the mixture was stirred at room temperature for 2 hours. The insoluble substance was filtered off and the filtrate was concentrated. To the residue was added 2 liters of water and the mixture was stirred, and then the precipitated crystals were filtered with suction. After the crystals were recrystallized from a mixture of ethyl acetate and methanol, 12.5 g of the purified crystals were redissolved in 350 ml of methanol under heating. To the solution was added 8 ml of 18% hydrochloric acid and the mixture was cooled with ice. The precipitated crystals were filtered with suction to give 1-benzyl-5-hydroxy-2-methyl-N-(1-(2-phenylethyl)-4-piperidyl)indole-3-carboxamide hydrochloride as white crystals, melting at 210°–212° C.

EXAMPLE 5

To a suspension of 10 g of 5-hydroxy-1-isopropyl-2-methyl-3-indolecarboxylic acid in 100 ml of ethyl acetate was added 15 ml of pyridine, and then to the mixture was added 10 ml of acetic anhydride. The whole mixture was stirred at room temperature for 3 hours. To the reaction mixture was added 200 ml of ice-cold water. After the mixture was acidified with 10% hydrochloric acid, the precipitated crystals were filtered and washed with water and then ethyl acetate to give 6.4 g of 5-acetoxy-1-isopropyl-2-methyl-3-indolecarboxylic acid. To a suspension of the compound in 100 ml of benzene was added 3 ml of thionyl chloride. After the mixture was refluxed for 3.5 hours, the solvent was distilled off. To the residue was added 50 ml of toluene and the mixture was concentrated. After the excess thionyl chloride was distilled off, the residual oil was dissolved in 100 ml of toluene. To the solution were added 5 g of 4-amino-1-(2-phenylethyl)piperidine and 10 ml of pyridine and the mixture was stirred at room temperature for 4 hours. After the completion of reaction, the crystals were filtered with suction, and washed with water and then ethyl acetate to give 8 g of 5-acetoxy-1-isopropyl-2-methyl-N-(1-(2-phenylethyl)-4-piperidyl)indole-3-carboxamide hydrochloride, melting at 242°–245° C. with decomposition.

To a solution of a total amount of the hydrochloride in 80 ml of methanol was added a solution of 2 g of sodium hydroxide in 10 ml of water, and the mixture was stirred for 10 minutes. After the methanol was concentrated, water was added to the residue to separate oil. To the oil was added 3 ml of glacial acetic acid and ethyl acetate, and the mixture was shaken well. The organic layer was washed with water and an aqueous solution of sodium hydrogencarbonate and the precipitated crystals were filtered. The crystals were dissolved in acetone containing ethanol and treated with concentrated hydrochloric acid to precipitate the corresponding hydrochloride. The crystalline hydrochloride was filtered and recrystallized from aqueous ethanol to give 5-hydroxy-1-isopropyl-2-methyl-N-(1-(2-phenylethyl)-4-piperidyl)indole-3-carboxamide hydrochloride, melting at 271°–276° C. with decomposition.

The following compounds can be prepared in a similar manner as above Examples 1 to 5:

(6) 5-Hydroxy-1-isobutyl-2-methyl-N-(1-(2-phenylethyl)-4-piperidyl)indole-3-carboxamide hydrochloride, melting at 270°–271° C. with decomposition (7) 5-Acetoxy-1-benzyl-2-pentyl-N-(1-(2-phenylethyl)-4-piperidyl)indole-3-carboxamide, melting at 165°–168° C.

(8) 1-Benzyl-5-hydroxy-2-pentyl-N-(1-(2-phenylethyl)-4-piperidyl)indole-3-carboxamide hydrochloride monohydrate, melting at 213°–215° C. with decomposition (9) 5-Acetoxy-1-hexyl-2-methyl-N-(1-(2-phenylethyl)-4-piperidyl)indole-3-carboxamide hydrochloride, melting at 230°–235° C.

(10) 1-Hexyl-5-hydroxy-2-methyl-N-(1-(2-phenylethyl)-4-piperidyl)indole-3-carboxamide hydrochloride monohydrate, melting at 238°–240° C.

(11) 5-Acetoxy-1-cyclohexyl-2-methyl-N-(1-(2-phenylethyl)-4-piperidyl)indole-3-carboxamide hydrochloride, melting at 258°–260° C. with decomposition

(12) 1-Cyclohexyl-5-hydroxy-2-methyl-N-(1-(2-phenylethyl)-4-piperidyl)indole-3-carboxamide hydrochloride hemihydrate, melting at 238°–242° C. with decomposition

(13) 1-(p-Fluorobenzyl)-5-hydroxy-2-methyl-N-(1-(2-phenylethyl)-4-piperidyl)indole-3-carboxamide, melting at 178°–181° C.

(14) 1-(p-Chlorobenzyl)-5-hydroxy-2-methyl-N-(1-(2-phenylethyl)-4-piperidyl)indole-3-carboxamide hydrochloride monohydrate, melting at 262°–265° C. with decomposition
(15) 1-Ethyl-5-hydroxy-2-methyl-N-(1-(2-phenylethyl)-4-piperidyl)indole-3-carboxamide, melting at 162°–165° C.
(16) 5-Hydroxy-2-methyl-1-(2-phenylethyl)-N-(1-(2-phenylethyl)-4-piperidyl)indole-3-carboxamide hydrochloride, melting at 142°–146° C.
(17) 5-Hydroxy-2-methyl-N-(1-(2-phenylethyl)-4-piperidyl)-1-(p-methylphenyl)indole-3-carboxamide hydrochloride, melting at 272°–276° C. with decomposition
(18) 5-Hydroxy-2-methyl-N-(1-(2-phenoxyethyl)-4-piperidyl)-1-phenylindole-3-carboxamide hydrochloride hemihydrate, melting at 162°–166° C.
(19) 5-Hydroxy-2-methyl-N-(1-(2-phenylethyl)-4-piperidyl)-1-(m-trifluoromethylphenyl)indole-3-carboxamide, melting at 209°–210° C.
(20) 5-Acetoxy-2-methyl-N-(1-(2-phenylethyl)-4-piperidyl)-1-(m-trifluoromethylphenyl)indole-3-carboxamide hydrochloride, melting at 285°–292° C. with decomposition
(21) 5-Acetoxy-1-(p-methoxyphenyl)-2-methyl-N-(1-(2-phenylethyl)-4-piperidyl)indole-3-carboxamide, melting at 194°–197° C.
(22) 5-Hydroxy-1-(p-methoxyphenyl)-2-methyl-N-(1-(2-phenylethyl)-4-piperidyl)indole-3-carboxamide hydrochloride, melting at 257°–262° C. with decomposition
(23) 5-Acetoxy-1-(p-chlorophenyl)-2-methyl-N-(1-(2-phenylethyl)-4-piperidyl)indole-3-carboxamide, melting at 172°–175° C.
(24) 1-(p-Chlorophenyl)-5-hydroxy-2-methyl-N-(1-(2-phenylethyl)-4-piperidyl)indole-3-carboxamide hydrochloride, melting at 256°–259° C. with decomposition
(25) 5-Acetoxy-2-methyl-1-phenyl-N-(1-(3-phenylpropyl)-4-piperidyl)indole-3-carboxamide, melting at 130°–133° C.
(26) 5-Hydroxy-2-methyl-1-phenyl-N-(1-(3-phenylpropyl)-4-piperidyl)indole-3-carboxamide hydrochloride monohydrate, melting at 162°–168° C.
(27) 5-Hydroxy-N-(1-(2-(p-methoxyphenyl)ethyl)-4-piperidyl)-2-methyl-1-phenylindole-3-carboxamide hydrochloride, melting at 258°–263° C. with decomposition
(28) 5-Acetoxy-2-methyl-N-(1-(2-phenylethyl)-4-piperidyl)-1-phenylindole-3-carboxamide, melting at 168°–171° C.
(29) 5-Hydroxy-2-methyl-N-(1-(2-phenylethyl)-4-piperidyl)-1-phenylindole-3-carboxamide hydrochloride, melting at 255°–258° C. with decomposition
(30) 5-Acetoxy-1-butyl-2-methyl-N-(1-(2-phenoxyethyl)-4-piperidyl)indole-3-carboxamide, melting at 139°–142° C.
(31) 1-Butyl-5-hydroxy-2-methyl-N-(1-(2-phenoxyethyl)-4-piperidyl)indole-3-carboxamide, melting at 124°–126° C.
(32) 5-Benzoyloxy-1-butyl-2-methyl-N-(1-(2-phenylethyl)-4-piperidyl)indole-3-carboxamide hydrochloride hemihydrate, melting at 192°–194° C.
(3) 1-Benzyl-2-methyl-N-(1-(2-phenylethyl)-4-piperidyl)-5-pivaloyloxyindole-3-carboxamide
(34) 1-Allyl-5-hydroxy-2-methyl-N-(1-(2-phenylethyl)-4-piperidyl)indole-3-carboxamide hydrochloride, melting at 269°–273° C.
(35) 5-Hydroxy-2-methyl-N-(1-(2-phenylethyl)-4-piperidyl)-1-propargylindole-3-carboxamide
(36) 1-Cyclohexylmethyl-5-hydroxy-2-methyl-N-(1-(2-phenylethyl)-4-piperidyl)indole-3-carboxamide
(37) 1-Cyclopropyl-5-hydroxy-2-methyl-N-(1-(2-phenylethyl)-4-piperidyl)indole-3-carboxamide
(38) 1-Benzyl-2-methyl-N-(1-(2-phenylethyl)-4-piperidyl)indole-3-carboxamide, melting at 177°–178° C.
(39) 1-Benzyl-N-(1-(2-phenylethyl)-4-piperidyl)indole-3-carboxamide hydrochloride, melting at 244°–247° C. with decomposition
(40) 1-Benzyl-5-fluoro-2-methyl-N-(1-(2-phenylethyl)-4-piperidyl)indole-3-carboxamide hydrochloride, melting at 254°–257° C. with decomposition
(41) 1-Benzyl-2,5-dimethyl-N-(1-(2-phenylethyl)-4-piperidyl)indole-3-carboxamide
(42) 1-Benzyl-5-methoxy-2-methyl-N-(1-(2-phenylethyl)-4-piperidyl)indole-3-carboxamide, melting at 196°–198° C.
(43) 1-Benzyl-5-benzyloxy-2-methyl-N-(1-(2-phenylethyl)-4-piperidyl)indole-3-carboxamide hydrochloride monohydrate, melting at 184°–189° C.
(44) 5-Hydroxy-1-isopropyl-2,6-dimethyl-N-(1-(2-phenylethyl)-4-piperidyl)indole-3-carboxamide hydrochloride hemihydrate, melting at 264°–269° C. with decomposition
(45) 1-Benzyl-5-hydroxy-2,7-dimethyl-N-(1-(2-phenylethyl)-4-piperidyl)indole-3-carboxamide
(46) 1-Benzyl-5-hydroxy-2-methyl-N-(1-(2-phenylethyl)-3-pyrrolidinyl)indole-3-carboxamide
(47) 1-Benzyl-5-hydroxy-2-methyl-N-(1-(2-phenylethyl)-4-hexahydroazepinyl)indole-3-carboxamide
(48) 6-Bromo-1-butyl-5-hydroxy-2-methyl-N-(1-(2-phenylethyl)-4-piperidyl)indole-3-carboxamide hydrochloride, melting at 263°–265° C.
(49) 1-Benzyl-6-chloro-5-hydroxy-2-methyl-N-(1-(2-phenylethyl)-4-piperidyl)indole-3-carboxamide
(50) 5-Hydroxy-1-isopropyl-6-methoxy-2-methyl-N-(1-(2-phenylethyl)-4-piperidyl)indole-3-carboxamide Although the present invention has been adequately discussed in the foregoing specification and examples included therein, one readily recognizes that various changes and modifications may be made without departing from the spirit and scope thereof.

What is claimed is:

1. A 3-indolecarboxamide compound of the formula:

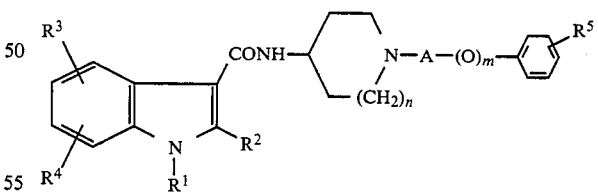

inclusive of compounds selected from the group consisting of pharmaceutically acceptable acid addition salt forms thereof, and hydrate forms thereof, wherein $R^1$ is a $C_{1-8}$ alkyl group, a $C_{3-8}$ cycloalkyl group, a $C_{3-8}$ cycloalkyl-$C_{1-8}$ alkyl group, an allyl group, a propargyl group, or a phenyl or phenyl-$C_{1-4}$ alkyl group which may be optionally substituted, on the benzene ring, by at least one substituent selected from the group consisting of a halogen atom, a trifluoromethyl group, a $C_{1-4}$ alkyl group and a $C_{1-4}$ alkoxy group; $R^2$ is a hydrogen atom or a $C_{1-6}$ alkyl group; $R^3$ is a hydrogen atom, a halogen atom, a $C_{2-6}$ alkanoyloxy group, a benzoyloxy group, a $C_{1-4}$ alkoxy group, a benzyloxy group, a hydroxyl group or a $C_{1-4}$ alkyl group; $R^4$ is a hydrogen atom, a halogen atom, a $C_{1-4}$ alkyl group, a $C_{1-4}$ alkoxy group or a hydroxyl group; $R^5$ is a hydrogen atom or a $C_{1-4}$ alkoxy group; A is an ethylene or trimethylene group, which may be optionally substituted by a $C_{1-4}$ alkyl group, n is zero, 1 or 2; and m is zero or 1.

2. The compound of the formula:

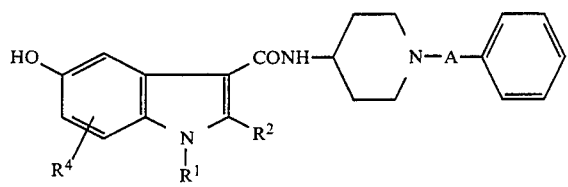

inclusive of compounds selected from the group consisting of pharmaceutically acceptable acid addition salt forms thereof and hydrate forms thereof, wherein $R^1$, $R^2$, $R^4$ and A are as defined in claim 1.

3. The compound of claim 2 wherein $R^2$ is a methyl group, $R^4$ is a hydrogen atom and A is an ethylene group.

4. The compound of claim 1:
1-Butyl-5-hydroxy-2-methyl-N-(1-(2-phenylethyl)-4-piperidyl)-indole-3-carboxamide, a pharmaceutically acceptable acid addition salt thereof or a hydrate thereof.

5. The compound of claim 1:
1-Benzyl-5-hydroxy-2-methyl-N-(1-(2-phenylethyl)-4-piperidyl)-indole-3-carboxamide, a pharmaceutically acceptable acid addition salt thereof or a hydrate thereof.

6. The compound of claim 1:
5-Hydroxy-1-isopropyl-2-methyl-N-(1-(2-phenylethyl)-4-piperidyl)indole-3-carboxamide, a pharmaceutically acceptable acid addition salt thereof or a hydrate thereof.

7. The compound of claim 1:
5-Hydroxy-2-methyl-1-(2-phenylethyl)-N-(1-(2-phenylethyl)-4-piperidyl)indole-3-carboxamide, a pharmaceutically acceptable acid addition salt thereof or a hydrate thereof.

8. The compound of claim 1:
5-Hydroxy-2-methyl-N-(1-(2-phenylethyl)-4-piperidyl)-1-phenylindole-3-carboxamide, a pharmaceutically acceptable acid addition salt thereof or a hydrate thereof.

9. A pharmaceutical composition for the prevention or treatment of allergic diseases containing an anti-allergic effective amount of the compound of claim 1 and a pharmaceutically acceptable carrier therefor.

10. The pharmaceutical composition of claim 9, wherein said allergic diseases are selected from the group consisting of asthma and allergic rhinitis.

11. The pharmaceutical composition of claim 9, wherein said anti-allergic effective amount ranges from 0.01 to 10 mg per kg.

* * * * *